United States Patent [19]

Faupel

[11] Patent Number: 5,715,821
[45] Date of Patent: Feb. 10, 1998

[54] NEURAL NETWORK METHOD AND APPARATUS FOR DISEASE, INJURY AND BODILY CONDITION SCREENING OR SENSING

[75] Inventor: Mark L. Faupel, Conyers, Ga.

[73] Assignee: Biofield Corp., Roswell, Ga.

[21] Appl. No.: 568,572

[22] Filed: Dec. 7, 1995

Related U.S. Application Data

[63] Continuation-in-part of Ser. No. 352,504, Dec. 9, 1994.
[51] Int. Cl.$^6$ ....................................................... A61B 5/05
[52] U.S. Cl. ...................... 128/653.1; 128/639; 128/734; 395/23; 395/2.41
[58] Field of Search ................................. 128/639, 733, 128/734, 653.1, 731, 920, 922; 364/413.02; 382/181, 209, 217, 218; 395/10, 11, 21, 23, 924, 2.41

[56] References Cited

U.S. PATENT DOCUMENTS

| | | |
|---|---|---|
| 4,094,307 | 6/1978 | Young, Jr. . |
| 4,112,491 | 9/1978 | Bugay . |
| 4,407,300 | 10/1983 | Davis . |
| 4,557,271 | 12/1985 | Stoller et al. . |
| 4,557,273 | 12/1985 | Stoller et al. . |
| 4,866,645 | 9/1989 | Lish . |
| 4,955,383 | 9/1990 | Faupel . |
| 4,993,423 | 2/1991 | Stice . |
| 5,099,844 | 3/1992 | Faupel . |
| 5,130,563 | 7/1992 | Nabet et al. . |
| 5,155,802 | 10/1992 | Mueller et al. . |
| 5,181,256 | 1/1993 | Kamiya . |
| 5,204,938 | 4/1993 | Skapura et al. . |
| 5,208,900 | 5/1993 | Gardner . |
| 5,311,876 | 5/1994 | Olsen et al. . |
| 5,320,101 | 6/1994 | Faupel et al. . |
| 5,325,862 | 7/1994 | Lewis et al. . |
| 5,417,211 | 5/1995 | Abraham-Fuchs et al. .......... 128/653.1 |
| 5,427,098 | 6/1995 | Faupel et al. . |
| 5,447,166 | 9/1995 | Gevins . |
| 5,509,103 | 4/1996 | Wang ....................... 395/2.41 |

Primary Examiner—Marvin M. Lateef
Assistant Examiner—Eleni Mantis Mercader
Attorney, Agent, or Firm—Sixbey, Friedman, Leedom & Ferguson PC; Daniel W. Sixbey

[57] ABSTRACT

A method and apparatus for disease, injury or condition screening or sensing wherein biopotentials are received from a plurality of measuring sensors located in the area of a suspected disease, injury or condition change site. These potentials are then processed and the processed values are provided to a particular type of neural network or a combination of neural networks uniquely adapted to receive and analyze data of an identifiable type to provide an indication of specific conditions.

17 Claims, 4 Drawing Sheets

NEURAL NETWORK METHOD AND APPARATUS FOR DISEASE, INJURY AND BODILY CONDITION SCREENING OR SENSING

This application is a continuation-in-part application of Ser. No. 08/352,504 filed Dec. 9, 1994.

TECHNICAL FIELD

The present invention relates generally to a method and apparatus for screening or sensing disease states, injury sites or bodily conditions in a living organism by detecting the DC biopotential of the electromagnetic field present between a reference and a plurality of test points on the living organism to measure the gradient of electrical activity which occurs as a function of biological activity.

BACKGROUND ART

In recent years the theory that measurement of the potential level of the electromagnetic field of a living organism can be used as an accurate screening and diagnostic tool is gaining greater acceptance. Many methods and devices have been developed in an attempt to implement this theory. For example, U.S. Pat. No. 4,328,809 to B. H. Hirschowitz et al. deals with a device and method for detecting the potential level of the electromagnetic field present between a reference point and a test point on a living organism. Here, a reference electrode and a test electrode provide DC signals indicative of the potential level of the electromagnetic field measured between the reference point and the test point. These signals are provided to an analog-to-digital converter which generates a digital signal as a function thereof, and a processor provides an output signal indicative of a parameter or parameters of the living organism as a function of this digital signal.

Similar biopotential measuring devices are shown by U.S. Pat. Nos. 4,407,300 to Davis, and 4,557,271 and 4,557,273 to Stroller et al. Davis, in particular, discloses the diagnosis of cancer by measuring the electromotive forces generated between two electrodes applied to a subject.

Often, the measurement of biopotentials has been accomplished using an electrode array, with some type of multiplexing system to switch between electrodes in the array. The aforementioned Hirschowitz et al. patent contemplates the use of a plurality of test electrodes, while U.S. Pat. Nos. 4,416,288 to Freeman and 4,486,835 to Bai disclose the use of measuring electrode arrays.

Unfortunately, previous methods for employing biopotentials measured at the surface of a living organism as a diagnostic tool, while basically valid, are predicated upon an overly simplistic hypothesis which does not provide an effective diagnosis for many disease states. Prior methods and devices which implement them operate on the basis that a disease state is indicated by a negative polarity which occurs relative to a reference voltage obtained from another site on the body of a patient, while normal or non-malignant states, in the case of cancer, are indicated by a positive polarity. Based upon this hypothesis, it follows that the detection and diagnosis of disease states can be accomplished by using one measuring electrode situated externally on or near the disease site to provide a measurement of the polarity of the signal received from the site relative to that from the reference site. Where multiple measuring electrodes have been used, their outputs have merely been summed and averaged to obtain one average signal from which a polarity determination is made. This approach can be subject to major deficiencies which lead to diagnostic inaccuracy, particularly where only surface measurements are taken.

First, the polarity of diseased tissue underlying a recording electrode has been found to change over time. This fact results in a potential change which confounds reliable diagnosis when only one external recording electrode is used. Additionally, the polarity of tissue as measured by skin surface recording is dependent not only upon the placement of the recording electrode, but also upon the placement of the reference electrode. Therefore, a measured negative polarity is not necessarily indicative of diseases such as cancer, since polarity at the disease site depends in part on the placement of the reference electrode.

When many electrodes are used to sense small DC biopotentials at the surface of the skin, such as in screening for breast cancer, it is crucial for the sensing electrodes to be accurately placed and spaced so that two adjacent electrodes are not overlapping or sensing the same test area. If these tolerances are not accurately maintained, false readings are likely to result.

As disease states such as cancer progress, they produce local effects which include changes in vascularization, water content, and cell division rate. These effects alter ionic concentrations which can be measured at the skin surface and within the neoplastic tissues. Other local effects, such as distortions in biologically closed electrical circuits, may occur. A key point to recognize is that these effects do not occur uniformly around the disease site. For example, as a tumor grows and differentiates, it may show wide variations in its vascularity, water content and cell division rate, depending on whether examination occurs at the core of the tumor (which may be necrotic) or at the margins of the tumor (which may contain the most metabolically active cells). The tumor may not respond significantly to growth factors, while the growth factors and the enzymes produced may significantly affect the normal cells surrounding the tumor. This fact was recognized by one of the present inventors, and his U.S. Pat. Nos. 4,995,383 and 5,099,844 disclose a method and apparatus which implement the principle that important electrical indications of disease are going to be seen in the relative voltages recorded from a number of sites at and near a diseased area, and not, as previously assumed, on the direction (positive vs. negative) of polarity.

Still, the accurate measurement of DC biopotentials for sensing or screening for disease, injury or bodily functions is very difficult to accomplish, for the DC potentials to be sensed are of a very low amplitude. Due to factors such as the low DC potentials involved and the innate complexity of biological systems, the collected data signals tend to include a substantial amount of noise which makes accurate analysis difficult. Also, biological systems are notorious for their complexity, nonlinearity and nonpredictability, and wide variations from the norm are not uncommon. Thus it is necessary to develop a method and apparatus for obtaining the necessary data from the measurement of biopotentials and then to extract and analyze pertinent information which is relevant to a condition under study.

DISCLOSURE OF THE INVENTION

It is a primary object of the present invention is to provide a novel and improved method and apparatus for condition screening or sensing wherein DC biopotentials from the area of a site on a living organism are measured and then processed in a neural network which has been taught to recognize information patterns indicative of a particular condition.

A further object of the present invention is to provide a novel and improved method and apparatus for disease, injury or bodily condition screening or sensing wherein DC biopotentials are received on separate channels from a plurality of sites at and near a suspected area of disease, injury or condition change on a living organism. A maximum potential differential is then obtained from the averages of multiple biopotential values taken over time and subsequently provided to a neural network which has been taught to recognize patterns indicative of a disease, injury or other bodily condition.

Yet a further object of the present invention is to provide a novel and improved method and apparatus for disease, injury or condition screening or sensing wherein DC biopotentials are received from a plurality of measuring sensors located in the area of a suspected disease, injury or condition change site. These potentials are then specifically provided to a particular type of neural network or a combination of neural networks uniquely adapted to receive and analyze data of an identifiable type to provide an indication of specific conditions.

Another object of the present invention is to provide a novel and improved method and apparatus for disease, injury or condition screening or sensing wherein differential values are derived from DC biopotentials located in the area of a suspected disease, injury, or condition change site. These potentials are then provided to a plurality of neural networks and the outputs of these neural networks are then used to provide an indication of specific conditions.

A still further object of the present invention is to provide a novel and improved method and apparatus for condition sensing or sensing wherein differential values are derived from DC biopotentials obtained from mirror image sensors located on the opposite breasts of a subject.

BEST MODE FOR CARRYING OUT THE INVENTION

Figure 1:
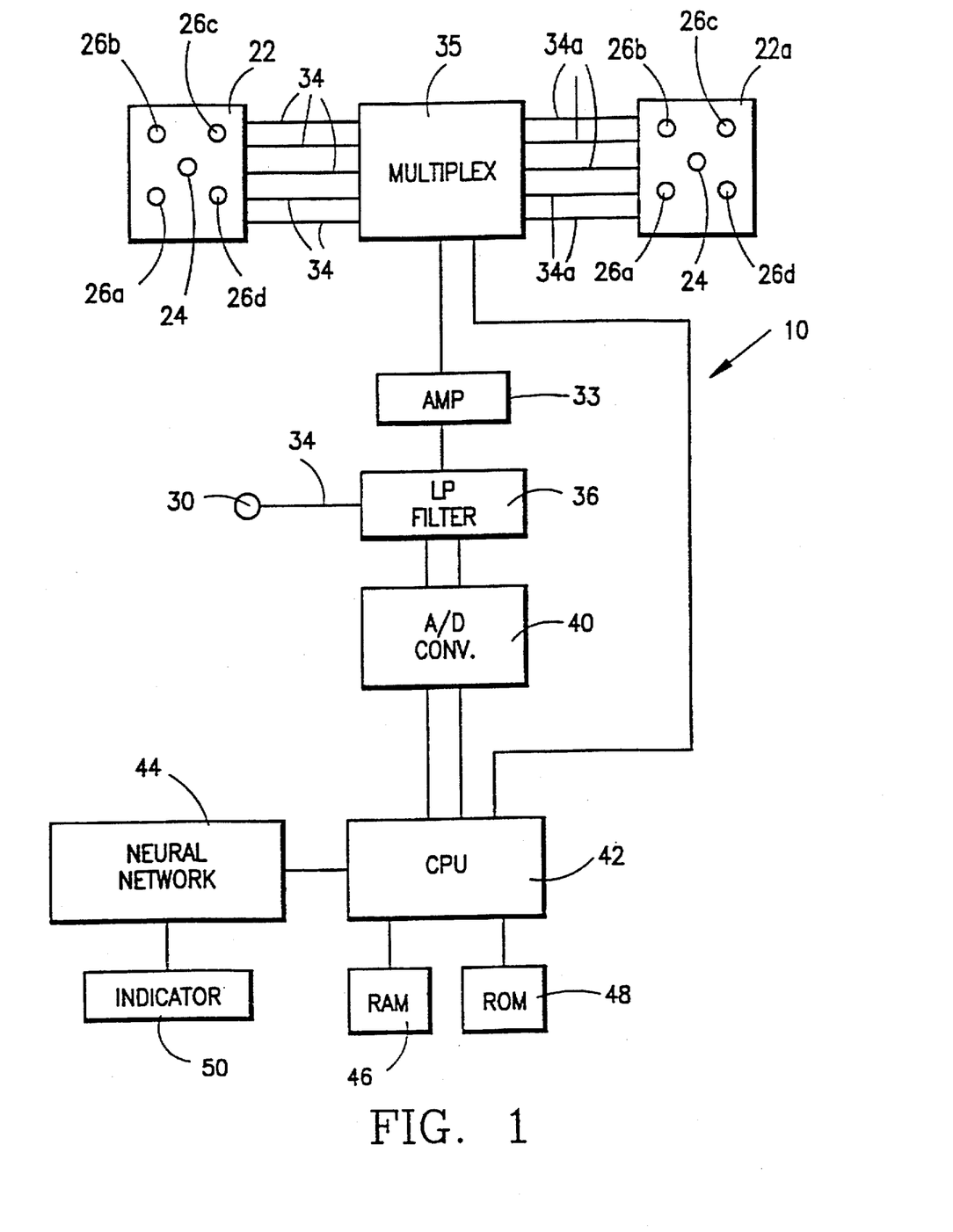
FIG. 1 is a block diagram of the general apparatus of the present invention.

FIG. 1 discloses a basic block diagram of an apparatus indicated generally at 10 for performing a discriminant analysis to obtain both raw data signals and differential signals for a pattern recognition device that then discriminates between patterns to achieve disease, injury or other condition screening or sensing. For purposes of illustration, the apparatus 10 will be described in connection with methods involving the screening for, or diagnosing of breast cancer. However, it should be recognized that the method and apparatus of the invention can be similarly employed for screening or diagnosis at other sites involving other conditions of a living human or animal. For example, the apparatus and method to be described can be used to detect disease conditions such as infection, ischemia, spasm, arthritis or other injury, or non-disease conditions such as ovulation, labor, abnormalities of labor, and fetal distress.

Figure 2:
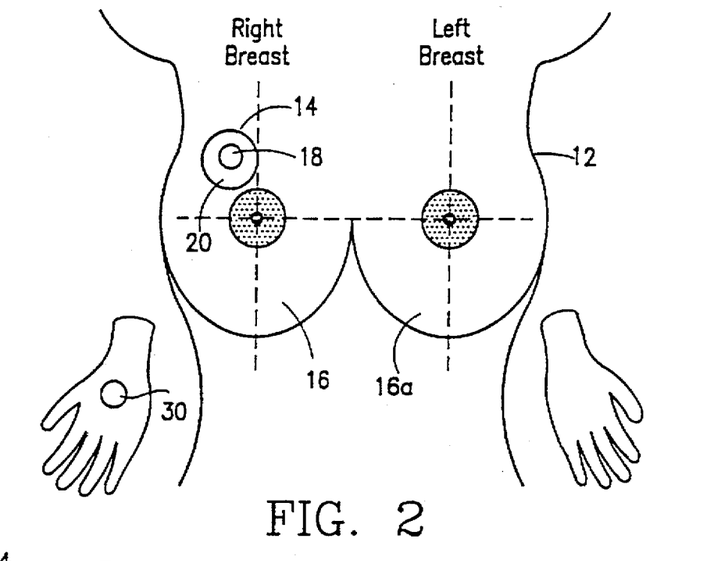
FIG. 2 is a diagram of the breasts of a human subject which receive the sensor arrays of FIG. 1.

In FIG. 2, a human subject 12 may have a cancerous lesion 14 on one breast 16. This cancerous lesion has a core 18 and an outer zone 20 surrounding the core where various differing local effects, such as changes in vascularization, water content and cell division rate occur. The outer zone 20 will include normal cells surrounding the lesion, for these cells often exhibit a much greater biopotential effect in response to tumor growth than does the actual tumor. Assuming first, for purposes of discussion, that the location of the lesion 14 is not known, and the device 10 is to be used to screen the breast 16 to determine whether or not a disease condition exists, skin surface potentials will be measured in an area of the breast, including the zone 20 using an electrode array 22 as shown in FIG. 1. The device and method of this invention contemplate the use of a variety of different sensor arrays and even the use of different types of sensors within an array depending upon the intended application for which the device 10 is used. For example, in the diagnosis of clinically symptomatic breast or skin lesions, the sensor array should cover various areas of the lesion as well as relatively normal tissue near the lesion site. For breast cancer screening (where patients are asymptomatic) the array should give maximum coverage of the entire breast surface. The aim in both of these cases is to measure the gradient of electrical activity which occurs as a function of the underlying biological activity of the organ system. The number of sensors used in the measurement will also be a function of specific application, and breast cancer screening may require the use of as few as twelve or as many as one hundred or more sensors 24 arranged on each breast 16 and 16a.

In breast cancer detection, one sensor array 22, as shown in FIG. 1, is used to obtain symptomatic breast differentials from a single breast, but two sensor arrays 22 and 22a are arranged on both breasts to obtain between the breast differential measurements.

For breast cancer screening, the sensors 24 and a central sensor 26 of an electrical array 22 should be mounted in a manner which permits the sensors to be accurately positioned against the curved surface of the breast 16 while still maintaining uniform spacing and the position of the sensors in a predetermined pattern. The sensor array 22 and the sensor arrays 22 and 22a are used in conjunction with at least one reference sensor 30, and all of these sensors are of a type suitable for detecting the potential level of the electromagnetic field present in a living organism.

Figure 3:
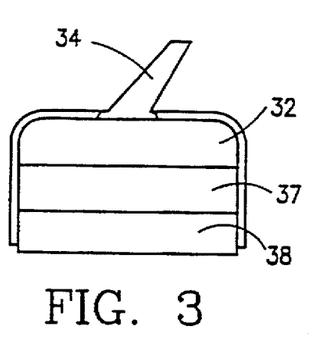
FIG. 3 is a generalized sectional diagram of the electrode which can be used as a sensor for the apparatus of FIG. 1.

In FIG. 3, an electrode for use as the sensors 24 and 30 is shown generally, and may include a layer of silver 32 having an electrical lead 34 secured in electrical contact therewith. In contact with the silver layer is a layer of silver chloride 37, and extending in contact with the silver chloride layer is a layer of ion conductive electrolyte gel or cream material 38 which contacts the surface of a living organism. This gel or cream, as will be subsequently indicated, is important in making a determination of the type of measurement to be taken.

The device 10 is a multi-channel device having electrical electrode leads 34 and 34a extending separately from the electrodes 24 and 26 to one or more solid state multiplexors 35. These multiplexors can, for example, be multiplexors designated as Harris Semiconductor Model H1-546-5. Each sensor array connected to the device 10, when in use, provides a plurality of outputs to a multiplexor connected to the array, and this multiplexor switches between the electrode leads 34 and 34a during a test period to connect the analog signals on each lead sequentially to a multiplexor output to create a time division multiplexed output. By providing one or more high speed solid state multiplexors for each array, it is possible to repeatedly sample biopotentials from a large number of sensors during a test period of minimal duration. The multiplexors 35 control whether signals will be received from only one breast 16 by means of the sensor array 22 or whether signals will be received from both breasts 16 and 16a by means of the sensor arrays 22 and 22a.

The outputs from the multiplexors 35 are amplified at 33 and provided to a low pass filter assembly 36 which operates to remove undesirable high frequency AC components which appear on the slowly varying DC voltage signal outputs provided by each of the sensors as a result of the electromagnetic field measurement. The low pass filter assembly 36 may constitute one or more multiple input low pass filters of known type which separately filter the signals on each of the input leads 34 and 34a when the array 22a is used, and then pass each of these filtered signals in a separate channel to a multiple input analog-to-digital converter 40. Obviously, the low pass filter assembly 36 could constitute an individual low pass filter for each of the specific channels represented by the leads 34 which would provide a filtering action for only that channel, and then each filtered output signal would be connected to the input of the analog-to-digital converter 40. For multiple channels, it is possible that more than one multiple input analog-to-digital converter will be used as the converter 40.

The analog-to-digital converter 40 converts the analog signal in each input channel to a digital signal which is provided on a separate output channel to the multiple inputs of a central processing unit 42. The central processing unit includes RAM and ROM memories 46 and 48. Digital input data from the analog-to-digital converter 40 is stored in memory and is processed by the CPU in accordance with a stored program to perform the sensing and scanning methods of the present invention.

The measurement data processed by the CPU 42 contains indications of the presence or absence of a disease or other body condition, such as a tumor, but those indications may not be readily discernable from a casual inspection of the data. Instead, analysis of the data is required, and it is imperative that this analysis yield results that are consistent and reliable. The collected data tends to be obscured by noise due to factors such as the low DC potentials involved and the innate complexity of biological systems. Biological systems are notorious for their complexity, and wide variances from the norm are not uncommon.

In order to accurately analyze the collected data in spite of the noise problem and the inherent nonlinearity of biopotential data, the present invention involves the use of at least one neural network 44 to examine the data developed by the CPU 42 and identify patterns indicative of the presence or absence of a disease or other condition. Essentially, the neural network is a processing system wherein a simulated set of connected processing elements (neurons) react to a set of weighted input stimuli. The output from these neurons bears a nonlinear relationship to the input signal vector, with the nature of the relationship being determined by the strength of the connections. The connection strengths between the neurons must be set to values appropriate to the problem solution, and this is done in an indirect fashion by having the network "learn" to recognize information patterns. Once this is accomplished, the network can be called upon to identify a pattern from a distorted facsimile of the same pattern.

For use with the present invention, it is desirable to employ a neural network having a learning capability which is separate from the normal network function for data analysis. This is desirable because otherwise the network would continue to learn and evolve as it is used, making validation of the results impossible. Known networks of this type are commercially available, such as a product identified as Neuro Shell II (Backpropogation) from the Ward Systems Group, Inc.

The network is first trained to recognize disease or other condition or injury patterns using data resulting from known studies. Subsequently during use, similar data derived by the CPU as a result of processing is then fed to the neural network 44, and the output of the neural network is directed to an indicator device 50 which may constitute a printer, a CRT display device, or a combination of such indicators. The indicator device 50 may incorporate computer technology and graphics capable of imaging, in at least two dimensions, the disease or injury condition indicated by the output from the neural network. Although the neural network 44 is shown as a separate block for illustrative purposes in FIG. 1, it may in fact constitute a function performed by software for the central processing unit 42.

The operation of the discriminant analysis device 10 will be clearly understood from a brief consideration of the method steps of the invention which the device is intended to perform. When the lesion 14 or other condition has not been identified and a screening operation is performed to determine whether or not a lesion or other condition is present, a screening sensor array 22 is positioned in place on the site being screened with the sensors 24, 26 positioned over various diverse areas of the site. If a breast 16 is screened, the sensor array will cover either the complete breast or a substantial area thereof. The reference sensor 30 is then brought into contact with the skin of the subject 12 in spaced relationship to the sensor array 22, and this reference sensor might, for example, be brought into contact with a hand of the subject. Then, the electromagnetic field between the reference sensor and each of the sensors 24, 26 is measured, converted to a digital signal and stored for processing by the central processing unit 42. The central processing unit controls the multiplexors 35, and the program control for the central processing unit causes a plurality of measurements to be taken over a period of time. Usually, measurements from individual sensors are taken sequentially and repetitively, but the measurements on all channels may be taken simultaneously and repetitively for the predetermined measurement time period.

In prior art units, a plurality of measurements have been taken over a period of time and often from a plurality of electrodes, but then these plural measurements are merely averaged to provide a single average output indication. In accordance with the method of the present invention, the measurement indications on each individual channel are not averaged with those from other channels, but are instead kept separate and averaged by channel within the central processing unit 42 at the end of the measurement period. For the duration of a single predetermined measurement period, for example, from sixteen measurement channels, the central processor will obtain sixteen average signals indicative of the average electromagnetic field for the period between the reference sensor 30 and each of the sensors in the sensor array 22 or the sensor arrays 22 and 22a. Of course, more reference sensors can be used, although only one reference sensor 30 has been shown for purposes of illustration.

Having once obtained an average signal level indication for each channel, the results of the measurements taken at multiple sites are analyzed in terms of a mathematical analysis to determine the relationships between the average signal values obtained. It has been found that the result of such an analysis is that a subset of relationships can be obtained which are indicative of the presence of a disease, injury or other body condition while a different subset might be obtained which will be indicative of the absence of these factors. Although either a discriminant mathematical analysis procedure or decision making logic may be designed to separately obtain and analyze the relationship between the average potential values in accordance with this invention for screening or diagnostic purposes, the discriminant mathematical analysis procedure to be hereinafter described in combination with data pattern recognition is a method which appears to be effective.

An important relationship to be obtained is often the maximum voltage differential (MVD), which is defined as the minimum average voltage value obtained during the measurement period subtracted from the maximum average voltage value obtained for the same period where two or more sensors are recording voltages from a test area. Thus, for each predetermined measurement period, the lowest average voltage level indication obtained on any of the channels is subtracted from the highest average voltage level indication obtained on any of the other channels to obtain an MVD voltage level. If this MVD voltage level is above a desired level >x, then a disease, injury or other condition, such as a malignancy, could be indicated. Similarly, if the average taken over the measurement period from one channel is an abnormally low value <y, the presence of this abnormally low individual sensor reading (IER) could be indicative of a disease, injury or other condition. These primary indicators may be further analyzed in accordance with a neural network control program to be subsequently described to reduce the number of false positive diagnosis, usually cases of non-malignant hyperplasia which may be falsely identified as cancer on the basis of high MVD or low IER readings.

When the device 10 is used in accordance with the method of the present invention for a screening function where a specific lesion 14 has not yet been identified, using as an example breast screening where the patient is asymptomatic, an array 22 is employed which will give maximum coverage of the entire breast surface. Then the MVD level, and possibly an IER level is obtained in accordance with the method previously described as well as the average values for each channel. All of this data, namely, the average values, and the MVD level is input to the neural network 44 which has been trained to discern a pattern from the data which is indicative of a disease condition. This same process can be performed with sensors of various types other than surface sensors, such as needle electrodes for invasive measurement and electrodes which measure resistance or impedance.

Figure 4:
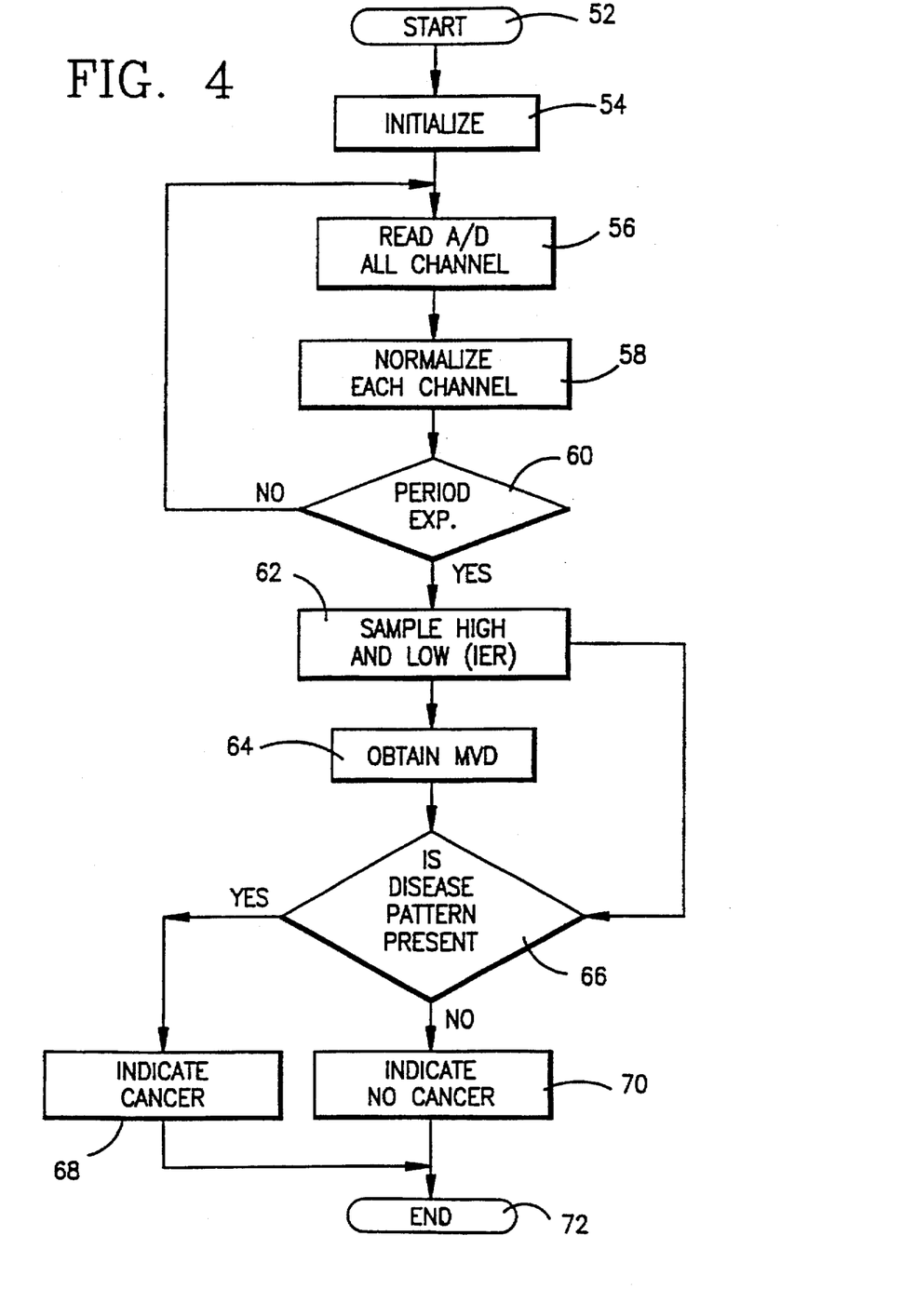
FIG. 4 is a flow diagram of the measurement operation of the apparatus of FIG. 1.

The general overall operation of the central processing unit 42 will best be understood with reference to the flow diagram of FIG. 4. The operation of the unit 10 is started by a suitable start switch as indicated at 52 to energize the central processing unit 42, and this triggers an initiate state 54. In the initiate state, the various components of the device 10 are automatically brought to an operating mode, with for example, the indicator 50 being activated while various control registers for the central processing unit are reset to a desired state. Subsequently, at 56, a predetermined multiple measurement period is initiated and the digital outputs which are either generated in the processing unit 42 or those from the analog-to-digital converter 40 are read. When an analog neural network 44 is employed, the analog values will be read at 56. The central processing unit may be programmed to simultaneously read all channel outputs but these channel outputs are usually sequentially read.

Once the analog or digital signals from all channels are read, an average signal for each channel is obtained at 58 for the portion of the measurement period which has expired. The average or normalized value for each channel is obtained by summing the values obtained for that channel during the measurement period and dividing the sum by the number of measurements taken. Then, at 60, the central processing unit determines whether the measurement period has expired and the desired number of measurements have been taken, and if not, the collection of measurement samples or values continues.

Once the measurement period has expired, the microprocessor will have obtained a final average value for each channel derived from the measurements taken during the span of the measurement period. From these average values, the highest and lowest average values obtained during the measurement period are sampled at 62, and at 64, and the lowest average channel value which was sampled at 62 is subtracted from the highest average channel value to obtain a maximum voltage differential value. Then both the channel average values from 62 as well as the maximum voltage differential value from 64 are directed as inputs to the neural network at 66 which has been trained to recognize disease patterns from such data. Alternatively, only the maximum voltage differential values from 64 are directed to the neural network 66.

In the neural network at 66, if a disease or other condition pattern is identified from the input MVD signal values or the MVD signal values and the average signal values, then a probably disease indication, such as cancer present, is provided at 68, but if a disease pattern is not recognized, then the lack of a probable disease condition is indicated at 70. Since neural networks generally provide a probability value, the probability of the presence or absence of a disease condition is indicated at 68 and 70, and the device may be used to distinguish high risk patients from low risk patients. After the indication of the probable presence or nonpresence of a disease at 68 or 70, the routine is ended at 72.

The neural network 66 may be used to recognize other patterns derived from the DC biopotential signals provided by the device 10. For example, there is a phasicity pattern which occurs in the averaged electrical biopotentials over time which can be sensed, and variations in this phasicity pattern may be recognized as indicative of particular disease, injury or other conditions. Another pattern can be recognized in the phasicity of the multiplicity of individual electropotential values which are obtained by the device 10 prior to averaging. During a test period, individual measurements in the hundreds will be taken from each sensor for averaging, and phasicity changes in these individual values provide a complex pattern which can be analyzed by the neural network. Changes in this complex phasicity pattern could be identified as indicative of certain disease, injury or other conditions. It is contemplated that a combined analysis may be made using the phasicity pattern of the biopotential signals before averaging or averaged signal values after averaging to obtain a combined analysis as an indicator of the presence or absence of a specific condition.

The apparatus for condition screening or sensing 10 of FIG. 1 may be either a digital or analog unit. For an analog unit, the analog to digital converter 40 is eliminated and the output of the low pass filter 36 is sent directly to the CPU 42 where the analog signals are averaged and an analog MVD is developed. These analog average and MVD signals are then provided as inputs to an analog neural network 44 rather than a digital network.

The apparatus for condition screening or sensing of the present invention may be used in a method for monitoring the efficacy of therapy for some diseases or injury conditions. A problem which arises in cancer treatment, for example, is assessing the efficacy of the treatment, whether it be by radiation or chemotherapy. However, the electrical biopotential differentials resulting from some cancers tend to change in response to chemotherapy. Thus once a cancer has been identified and an initial MVD level for that particular cancer has been computed, subsequent MVD levels are taken as treatment progresses and compared to previous MVD levels to determine whether or not a change is occurring. Depending upon the treatment in progress, a change, or in some instances a lack of change in the MVD level will tend to indicate that a therapy treatment is positive and is having some success.

Other conditions of the human body may also be effectively monitored using the method and apparatus of the present invention. For example, in females during ovulation, tissue rupture occurring incident to passage of the ova to the fallopian tubes results in significantly altered biopotential levels which can be sensed. Symptoms caused by ovulation can be confused with those associated with appendicitis, but the high MVD levels resulting from ovulation can be used to differentiate between the two.

The efficacy of a variety of therapeutic treatments, such as post menopause hormone therapy and various immunal therapies may also be monitored using the method and apparatus of the present invention.

The use of the device and method of the present invention to provide an objective test for ovulation will be extremely useful in the prevention of an unwanted pregnancy as well as an aid in assisting women who are experiencing difficulties with infertility.

Another normal bodily function associated with DC biopotentials is labor or uterine contractions related to the birth of a child. The measurement of DC biopotentials in accordance with the present invention during the occurrence of these conditions can be used to determine the effectiveness of the contractions in leading to cervical dilation and the probability of a normal vaginal delivery. Also, DC electrical biopotential measurements can be useful in distinguishing normal from abnormal delivery patterns as well as in the detection of fetal distress and abnormalities of labor such as separation of the placenta prematurely or infraction of the placenta.

The employment of a plurality of sensors 24, 26, 30 for the measurement of bioelectric phenomena means that a nearly limitless number of differentials can be calculated. Early investigations of this phenomena focused on two general classes of differentials; Symptomatic (within) breast differentials and Between-Breast Differentials. The Symptomatic (within) breast differential was obtained using one or more sensor arrays 22 on a single breast 16 which contains a suspicious lesion in the manner described, while the Between-Breast Differentials were obtained using sensor arrays 22 and 22a on the breasts 16 and 16a. The Between-Breast Differential obtained was the difference between the symptomatic breast differential and the asymptomatic breast differential; the asymptomatic breast being the breast 16a which does not include a suspicious lesion. Once the symptomatic and asymptomatic breast differential were obtained by the central processor unit 42 using the procedure of FIG. 4 to obtain an MVD for each breast, the processor then compares the asymptomatic and symptomatic differentials to obtain the difference therebetween as a Between-Breast differential.

With the advent of more precise measurement sensors for DC biopotentials, additional, more precise differentials can be calculated to reveal more about a given disease state. An example of one such differential developed in accordance with this invention is the Mirror-Image differential, in which differences between the corresponding, mirror image sensors are calculated; for example between the sensor placed in the upper outer quadrants of each breast. These can then be averaged to produce a more precise indicator of between-breast asymmetry. This is opposed to the antecedent Between Breast Differentials which calculated this asymmetry as the difference between the within breast differentials of both breasts.

Mirror-Image differential measurement is a more sensitive indicator of between breast symmetry, as it provides differentials from individual areas of both breasts rather than an overall differential for the complete breasts. With a between breast differential, if there is a lesion on the asymptomatic breast which was unknown, the differential value is significantly affected. With Mirror Image differential measurements, the differentials obtained from areas removed from the unknown lesion on the asymptomatic breast may not be significantly affected by the lesion.

To obtain the Mirror-Image differential, multiple measurements are taken from corresponding sensors (i.e. 26b) in the sensor arrays 22 and 22a under the control of the central processor 42. These multiple measurement values are averaged for each sensor by the central processor, and then a difference value is obtained from the averages for the two sensors by the central processor. This process is continued until differentials are obtained for all mirror image sensor pairs, and then these differentials are averaged by the central processor to obtain a final mirror image differential.

The mirror image differential or the between breast differential for each test period can be provided by the central processor as a processed signal value to an appropriate neural network of the types to be described.

Another class of variables which may improve disease detection are those which compress the differential by making it conform to a known distribution. This is useful especially when maximum differentials are calculated from many data points, which may contain an outlier. By imposing a known distribution on the set of data points, such as the Bienayme-Tschebycheff or Cramer distribution, the effect of statistical outliers can be diminished.

Still another approach to gain additional information from bioelectric measurements is to weight the differentials by the distance between the sensors. Other manipulations which may reduce noise in bioelectric differentials are normalizing procedures, by which the range of differentials in the symptomatic breast 16 is evaluated and constrained in terms of the range of differentials in the opposite breast 16a.

Clinical studies have indicated that the relative effectiveness of the electrolyte gel or cream 38 used as an electroconductive medium in skin sensor electrodes 24,26,30, relates to the types of variables employed in disease detection. For example, if the sensor type is kept constant, more effective discrimination of disease state for gel-containing sensors is afforded by employing within breast differentials, such as the maximum difference between five sensors which are located in a quadrant of the breast with a suspicious lesion. On the other hand, sensors loaded with an electroconductive cream rely more on differentials between the two breasts, such as the set of mirror-image differentials described above. For these types of sensors, differentials calculated from sensors located at some distance away from each other tend to give better diagnostic information than differentials calculated from sets of sensors placed more closely together, such as the within quadrant differential found effective for gel loaded sensors. The differentials used for disease discrimination should be tuned to the type of sensor employed.

A number of different techniques may be employed in accordance with the present invention for deconvolving bioelectric measurements recorded from living organisms. The techniques described result from the complexity of data generated by devices specifically designed to record bioelectric information from a plurality of points on an organism, and/or from a plurality of measurements made over time from at least one biosensor in contact with an organism, either internally or on the skin surface. The advantages of these techniques for the intended applications are that they do not assume the shape of the distribution of data, that is, they are effective for both linear and nonlinear systems. Biological systems, including bioelectric fields, which are notorious for their nonlinearity and nonpredictiveness are best analyzed using the distribution-independent techniques to be hereinafter described. Often, the technique employed is dependent upon a number of variables, such as the type of biosensor used and the type and volume of data to be analyzed.

As previously indicated, in artificial neural networks, data can be processed by several layers of interacting decision points or neurons. The network "learns" to recognize patterns from input data to produce a predictive output, such as benign vs. malignant breast disease. There are several varieties of artificial neural networks which have been found to have specific utility for condition sensing using the apparatus 10 of FIG. 1. These networks are operative with a variety of one or more types of measurements provided by the apparatus 10. The input to these networks can be maximum voltage differentials, channel averages, between breast differentials, mirror image differentials, and in some instances, raw unaveraged biopotential measurements.

Figure 5:
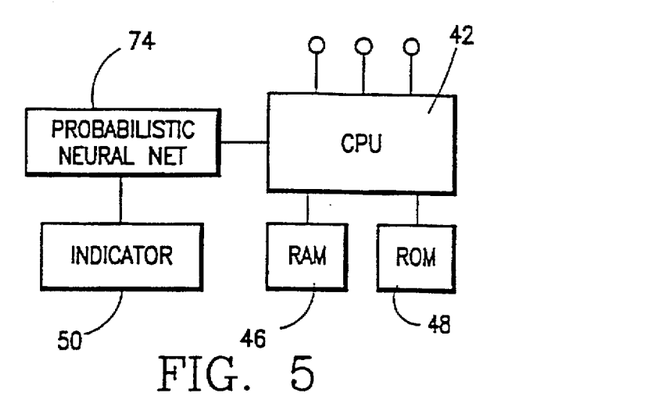
FIG. 5 is a block diagram of a probabilistic neural network used with the apparatus of FIG. 1.

Referring now to FIG. 5, when the apparatus 10 of FIG. 1 is used to obtain the somewhat limited data derived from a subject during a single test or group of tests taken during a single test period, the neural network 44 should consist of a probabilistic neural network 74. Probabilistic neural networks produce probability values ranging from 0.00 to 1.00 as to whether a given disease state exists. The probabilistic neural networks learn quickly and do not require large amounts of data. They function well in situations where the output is bimodal, for example, cancer vs. benign disease states. In order to produce a predictive probabilistic neural network, data is divided into three sets; the learning set, the test set, and the production set. Typically, 80 percent of the data is used in the learning set, 10 percent in the test set, and 10 percent in the production set. The probabilistic neural network identifies bioelectric patterns associated with benign vs. malignant disease states using the learning set. The predictiveness of the probabilistic neural network is monitored and altered periodically by comparison with the test set, and the final network is then checked for predictive accuracy against the production set. A key point for developing predictive probabilistic neural networks is the distribution of cases which make up the three data sets. For biopotentials, the most predictive probabilistic neural networks require that a relatively large proportion of data cases be reserved for the test and production sets (at least 20 percent for each set). This is most likely due to the fact that probabilistic neural networks are highly data driven (i.e., training set probabilistic neural networks don't necessarily transfer to new data) if given the large number of variables (e.g., surface electrical potential differentials) generated by multi-sensor arrays.

As opposed to probabilistic neural networks in which the output typically is bimodal, general regression neural networks are specifically developed to handle continuous variable outputs. Because of this, they tend to require relatively large mounts of data. An application of a general regression neural network would be in identifying a set of bioelectric variables which correlate with a continuous measure of disease state or cell proliferation such as Thymidine Labeling Index, a continuous variable which ranges from 0.0 to about 15.0. Similarly, backpropogation neural networks require relatively large amounts of data to generate predictive patterns. They differ from other types of neural networks because of the degree of complexity between the various levels of neurons and their interconnections. Backpropogation neural networks tend to generalize well to (predict for) new sets of data. For this reason, they can be effective for bioelectric information, especially if large amounts of data are available.

Figure 6:
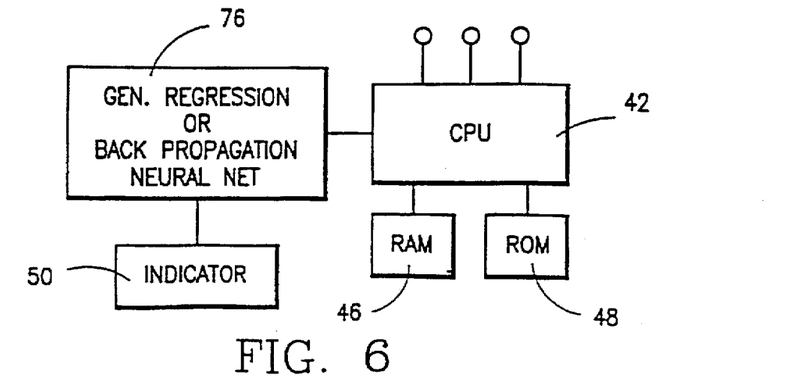
FIG. 6 is a block diagram of a general regression and neural network used with the apparatus of FIG. 1.

In instances where the apparatus 10 of FIG. 1 is used to collect differentials from a multiplicity of tests taken over an extended period of time and this data is then stored and later reentered in the central processor unit 42, the neural network 44 will be either a general regression or a backpropogation neural network as indicated at 76 in FIG. 6. An advantage of these neural networks 76 is their ability to identify intermediate disease states on the basis of biologic electromagnetic fields. As opposed to artificial intelligence paradigms, such as classification and regression trees, the neural networks 76 can provide an output on a scale of continuous values. Since disease states also lack the arbitrary black and white nature sometimes imposed by statistical reduction, these neural networks may be a better approximator of actual disease progression. For example, the progression of a tissue or an organ system from a normal state to malignant state is not saltatory; rather the tissue goes from normal through various pre-malignant stages until frank cancer is discovered. Thus there exist "shades of grey" in the progression of certain diseases. The neural networks 76, when coupled with fuzzy logic or other model-free methods of estimation or approximation, may provide a better means to discriminate the normal state from early disease, or early disease from later disease.

In fuzzy systems, rules in an algorithm are defined as any number of "patches" which cover events in a nonlinear system. In terms of disease states, the events could be defined as various stages along the continuum from normal to malignant. The "patches" would be the bioelectric measurements which define the set of disease states in the continuum. In fuzzy systems, all of the input rules are activated simultaneously, with different weights, to define a disease state. This can result in improved clinical utility in the following way. Various cut-off values in the neural net result can be stored in the central processor unit 42 and used to make determinations regarding patient management. For example, cutoffs could be established at 0.25, 0.50, and 0.75. Patients with less than 0.25 could be relatively assured they are free of serious disease, patients between 0.25 and 0.50 could be monitored by follow-up, patients between 0.50 and 0.75 could be monitored using additional tests while patients higher than 0.75 could be advised to proceed directly to biopsy. In this way, cost effective triaging of patients could occur.

Commercial versions of the probabilistic, general regression and backpropogation neural networks which can be used with this invention are available from Ward Systems Group Inc. of Frederick, Md., and are designated as Neuro Shell 2, Release 2.0.

All of the pattern recognition strategies discussed above are approximations of real world phenomena. As such, each has its own set of advantages and disadvantages as estimators of actual biologic functions and disease states. Given this, the optimal approach to disease detection by pattern recognition of bioelectric fields might lie in combining various pattern recognition strategies in novel ways. For example, artificial neural networks are reputed to be analogs of brain function. However, in recognizing patterns, the brain probably uses a combination of digital and analog strategies. By combining the outputs of several artificial neural networks in a classification tree or entropy pattern, it is possible to more closely match patterns with disease states.

Figure 7:
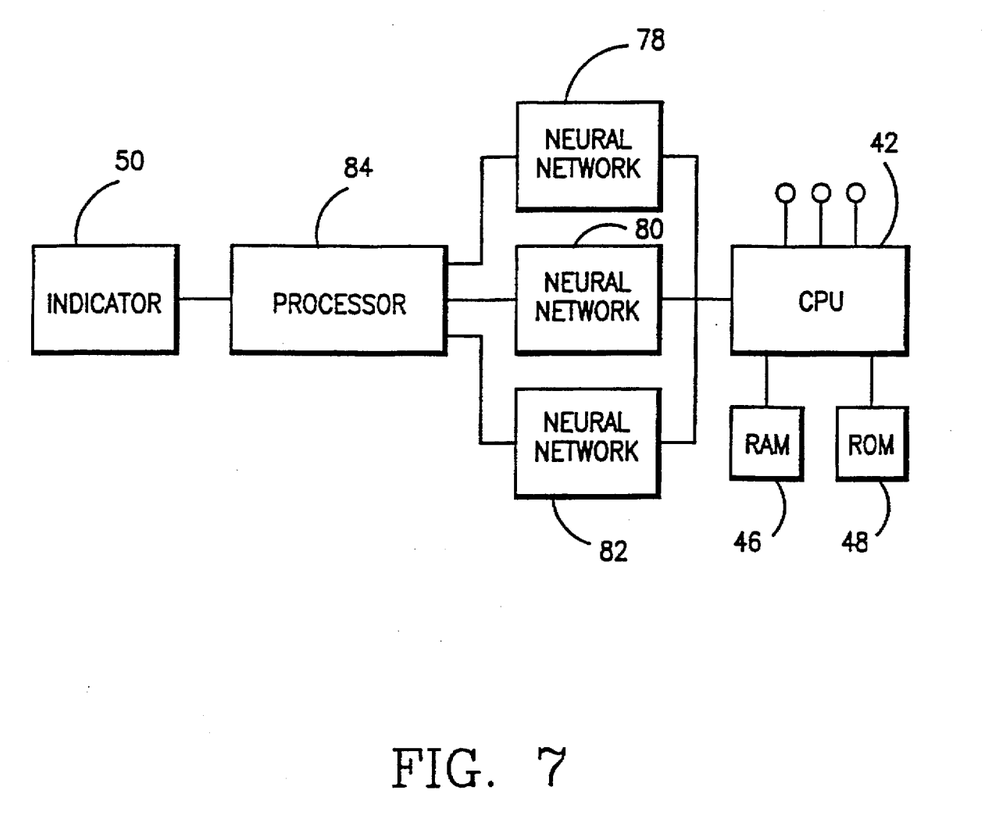
FIG. 7 is a block diagram of a plurality of neural networks used with the apparatus of FIG. 1.

With reference to FIG. 7, a plurality of separate neural networks 78, 80 and 82 are connected to separately process the differentials from the central processor unit 42. Depending on the volume of data input to the central processor, these plural neural networks may be the networks 74 or 76. The outputs of these neural networks are then input to a processor 84 which may actually be a separate processor or a portion of the central processor unit 42. The processor 84 may include an entropy minimax program which operates on the basis of minimal information entropy. Commercial versions which apply the entropy minimax theory to applied pattern recognition are available from Entropy Ltd. of Lincoln, Mass. under the designation entropy minimax. The entropy minimax form of pattern recognition is similar mathematically to thermodynamic entropy, hence its name. The aim of the entropy minimax program is to identify sets of variables or events which predict a state on the basis of minimal information entropy. Entropy minimax recognition can be understood as a process by which multivariate data is partitioned into n sets, each of which corresponds to a disease state. The members of the set are all possible unique vectors (combinations) of attribute values (variables) which may be created from the attribute list. The partitioned sets are created by finding the subset of data having the least entropy (or most predictive pattern). Having found that subset, it removes those cases from further consideration, and moves on to the next subset with the least amount of entropy. These successive identifications of sets proceed until all the cases are accounted for. This approach lies somewhere in between classification tree analysis and artificial neural networks in that although the sets of data are discrete (as in a decision tree) the weights placed on the variables are done so simultaneously (as in artificial neural networks).

Another way in which the various pattern recognition strategies could be combined would be to have the processor 84 weight the values from the three neural networks 78, 80 and 82 to obtain a final disease classification. For example, the value used for a final disease classification might be the value closest to that provided by a majority of the neural networks or, alternatively, might be an average value derived from the plural neural network outputs.

I claim:

1. An apparatus for sensing a condition at test sites which are the right and left breasts of a human subject by measuring electrical biopotentials which are a function of the electromagnetic field present at each said test site comprising:

an electrode sensing assembly operative during a test period to detect biopotentials indicative of said electromagnetic field and provide output test potentials which includes at least two biopotential sensor arrays adapted for contact with the subject to detect biopotentials present in the area of said test sites and to provide test potentials as a function of said detected biopotentials, said electrode sensing assembly including at least one biopotential reference sensor, and at least a first sensor array including a plurality of biopotential test sensors adapted to contact the right breast of the subject and a second sensor array including a plurality of biopotential test sensors adapted to contact the left breast of the subject, and a test processor connected to receive said test potentials provided by said sensor arrays and to provide processed potentials therefrom, a plurality of neural networks each programmed to detect a pattern of potentials indicative of the presence of said condition, said neural networks each operating to receive said processed potentials and to provide an output value indicative of the presence or absence of said condition, and a neural network processor connected to receive the output values from said neural networks, and operating to weight said output values to obtain a condition indication.

2. The apparatus of claim 1 wherein each said first and second sensor array includes a plurality of test sensors, each said test sensor operating with a reference sensor to detect biopotentials which are present in the area of a test site and to provide output test potentials as a function thereof, said test processor operating during a test period to receive a plurality of test potentials from each of a plurality of test sensors and to average the test potentials from each said test sensor to obtain a plurality of averaged potentials with one average potential for each said test sensor, the test processor further operating to compare said plurality of averaged potentials to obtain a maximum and a minimum average potential therefrom and to subsequently obtain a differential value indicative of the difference between said maximum and minimum average potentials and to provide said differential value to said neural networks.

3. The apparatus of claim 1 wherein said neural network processor averages said output values.

4. An apparatus for sensing a condition by measuring electrical DC biopotentials at test sites on the right and left breasts of a human subject comprising:

an electrode sensing assembly operative during a test period to detect DC biopotentials and provide output test potentials which includes at least one biopotential reference sensor and at least a first sensor array including a plurality of biopotential test sensors adapted to contact a test site on the right breast of a subject and a second sensor array including a plurality of biopotential test sensors adapted to contact a test site on the left breast of a subject, each said test sensor in said first and second sensor arrays operating with a reference sensor to detect D.C. biopotentials which are present in the area of a test site and to provide output test potentials as a function thereof, a processor means connected to receive said test potentials and operating during a test period to receive a plurality of output test potentials from each of a plurality of test sensors in said first and second sensor arrays and to average the output test potentials from each said test sensor to obtain an average potential value for each test sensor in said first sensor array and an average potential value for each test sensor in said second sensor array, the processor means operating to compare said average potential values from said first sensor array to obtain a first maximum and a first minimum average potential value therefrom and to subsequently obtain a first differential value indicative of the difference between said first maximum and first minimum average potential values for said right breast and to compare said average potential values from said second sensor array to obtain a second maximum and a second minimum average potential value therefrom and to subsequently obtain a second differential value indicative of the difference between said second maximum and second minimum average potential values for said left breast, said processor means further operating to compare said first and second differential values to obtain a between breast difference value indicative of the difference between said first and second differential values, and a neural network programmed to detect breast difference values indicative of the presence of said condition, said neural network being connected to receive said between breast difference value and operating to provide an output indicative of the presence or absence of said condition.

5. The apparatus of claim 4 wherein the test sensors of said first and second sensor arrays and said biopotential reference sensor are substantially identical biopotential sensing electrodes, each such biopotential sensing electrode including an electroconductive gel for contacting the human subject, and said neural network is a probabilistic neural network.

6. An apparatus for sensing a condition by measuring electrical D.C. biopotentials at test sites on the right and left breasts of a human subject comprising:

an electrode sensing assembly operative during a test period to detect D.C. biopotentials and provide output test potentials which includes at least one biopotential reference sensor and at least a first sensor array including a plurality of biopotential test sensors adapted to contact a test site on the right breast of a subject and a second sensor array including a plurality of biopotential test sensors adapted to contact a test site on the left breast of a subject, each said test sensor in said first and second sensor arrays operating with a reference sensor to detect D.C. biopotentials which are present in the area of a test site and to provide output test potentials which are a function thereof, each test sensor in said first sensor array being arranged relative to the remaining test sensors in said first sensor array for contact with a specific test area on said right breast and having a corresponding mirror image test sensor in said second sensor array for contact with a test area on said left breast corresponding to said specific test area on said right breast,, a processor means connected to receive said test potentials and operating during a test period to receive a plurality of test potentials from each test sensor on the right breast and from the mirror image test sensor therefor on the left breast and to average the test potentials from each said right breast test and left breast mirror image sensor therefor to obtain an average value from each, the processor means further operating to compare the average value from each right breast test sensor with the average value from each mirror image left breast test sensor to obtain a difference value indicative of any difference therebetween and to average the difference values so obtained to provide a mirror image differential value, and a neural network programmed to detect mirror image differential values indicative of the presence of said condition, said neural network being connected to receive said mirror image differential value and operating to provide an output indicative of the presence or absence of said condition.

7. The apparatus of claim 6 wherein the test sensors of said first and second arrays and said biopotential reference sensor are substantially identical biopotential sensing electrodes, each such electrode including an electroconductive cream for contacting the human subject, and said neural network is a probabilistic neural network.

8. The apparatus of claim 6 wherein said processor means operates to provide said mirror image differential value to a plurality of probabilistic neural networks.

9. An apparatus for sensing a condition at test sites on the right and left breasts of a human female subject by measuring DC electrical biopotentials which are a function of the electromagnetic field present at each said test site comprising:

an electrode sensing assembly operative during a test period to detect DC biopotentials indicative of said electromagnetic field and provide output test potentials, which includes biopotential sensors adapted for contact with the subject to detect DC biopotentials present in the area of a test site and to provide test potentials as a function of said detected DC biopotentials, said electrode sensing assembly including at least one biopotential reference sensor, and at least a first sensor array including a plurality of biopotential test sensors adapted to contact the right breast of the subject and a second sensor array including a plurality of biopotential test sensors adapted to contact the left breast of the subject, each said test sensor in said first and second sensor arrays operating with a reference sensor to detect DC biopotentials which are present in the area of a test site and to provide output test potentials as a function thereof, each sensor in said first sensor array being arranged relative to the remaining sensors in said first sensor array for contact with a test area on said right breast and having a corresponding mirror image sensor in said second sensor array for contact with a corresponding test area on said left breast, each sensor in said second sensor array being arranged relative to the remaining sensors in said second sensor array for contact with test areas on said left breast which correspond with test areas on said right breast contacted by the sensors in said first sensor array, and a processor operating during a test period to receive a plurality of test potentials from each test sensor on the right breast and from the mirror image test sensor on the left breast and to average the test potentials from each said right breast test and left breast mirror image sensor to obtain an average value from each, the processor further operating to compare the average value from each right breast test sensor with the average value from each mirror image left breast sensor to obtain a difference value therefrom and to average the difference values so obtained to provide a mirror image differential value.

10. A method for sensing a condition at a test site on a human or animal subject as a function of biopotentials indicative of an electromagnetic field present in the subject, said method comprising:

detecting respective biopotentials indicative of the electromagnetic field present in said subject at each of a plurality of measurement locations located in an area of the test site and at least one reference location on the subject, processing said detected biopotentials to obtain a plurality of biopotential measurement values for each such location, programming a plurality of probabilistic neural networks to detect biopotential patterns indicative of said condition and to provide a bimodal output indicative of the presence or absence of said condition, providing said plurality of biopotential measurement values to said plurality of probabilistic neural networks and weighting the bimodal outputs of said plurality of neural networks to obtain a condition indication.

11. The method of claim 10 which includes averaging the outputs from the plurality of neural networks.

12. The method of claim 10 which includes selecting a value for condition classification which is within a range of values provided by a majority of said neural networks.

13. A method for sensing a condition by measuring DC biopotentials at identical test sites on a right breast and a left breast of a human female subject, said method comprising:

arranging a first plurality of right breast DC biopotential sensors at spaced locations on the test site on the right breast of the subject, arranging a second plurality of left breast DC biopotential sensors on the test site on the left breast of the subject, each such left breast biopotential sensor in said second plurality of DC biopotential sensors constituting a mirror image sensor for a corresponding right breast sensor in said first plurality of DC biopotential sensors, locating each mirror image left breast sensor at a location on the test site on the left breast which corresponds to the location of the corresponding right breast sensor on the right breast, obtaining during a test period a plurality of biopotential measurements from each right breast sensor and from the mirror image left breast sensor, averaging the biopotential measurements taken from each right breast sensor and each mirror image left breast sensor to obtain an average value for each, comparing the average value from each right breast sensor with the average value from the mirror image left breast sensor to obtain a difference value therebetween, averaging the difference values obtained from all right breast sensors and mirror image left breast sensors to obtain a mirror image differential value, and using said mirror image difference value to determine the presence or absence of said condition.

14. An apparatus for sensing a disease condition and the progression of the condition at a test site on a human or animal subject by measuring electrical D.C. biopotentials present at said test site comprising:

an electrode sensing assembly operative during a test period to detect D.C. biopotentials and provide output test potentials which are a function thereof, said electrode sensing assembly including at least one reference sensor for contact with the subject and at least one sensor array including a plurality of test sensors for contact with the test site, each said test sensor operating with a reference sensor during a test period to detect D.C. biopotentials present in an area of the test site and to provide output test potentials as a function thereof, conversion means to receive and convert each test potential to a digital test signal which is a function of said test potential, a processor connected to said conversion means to receive said digital test signals therefrom, said processor operating during a test period to receive a multiplicity of digital test signals for each of said test sensors and to average the digital test signals from each said test sensor to obtain an average value therefrom for each said test sensor at the end of a test period, the processor operating to compare the average values obtained for all test sensors to obtain a maximum and a minimum average value and subsequently to obtain a differential value for a test period indicative of the difference between said maximum and minimum average values, storage means connected to said processor, said processor operating to initiate a multiplicity of test periods over an extended time period and to store each differential value obtained from each test period in said storage means, and at least one neural network connected to said processor and programmed to identify a set of electromagnetic variables which correlate with a continuous measure of disease state, said processor operating at the end of the extended time period to provide said stored differential values to said at least one neural network.

15. The apparatus of claim 14 which includes a plurality of neural networks connected to said processor, said processor operating to provide said stored differential values to each of said neural networks.

16. The apparatus of claim 14 wherein said neural network is a general regression neural network.

17. The apparatus of claim 14 wherein said neural network is a backpropagation neural network.

* * * * *